United States Patent [19]

Eue et al.

[11] Patent Number: 4,457,774
[45] Date of Patent: Jul. 3, 1984

[54] SELECTIVELY HERBICIDAL 4-AMINO-6-TERT.-BUTYL-3-ETHYLTHIO-1,2,4-TRIAZIN-5(4H)-ONE

[75] Inventors: Ludwig Eue, Leverkusen; Robert Schmidt, Berg-Gladbach; Karlfried Dickoré, Leverkusen, all of Fed. Rep. of Germany

[73] Assignee: Bayer Aktiengesellschaft, Leverkusen, Fed. Rep. of Germany

[21] Appl. No.: 303,658

[22] Filed: Sep. 18, 1981

[30] Foreign Application Priority Data

Nov. 4, 1980 [DE] Fed. Rep. of Germany ....... 3041587

[51] Int. Cl.³ .............................................. A01N 43/64
[52] U.S. Cl. .......................................... 71/93; 71/92; 71/100; 71/108; 71/111
[58] Field of Search ............................................ 71/93

[56] References Cited

U.S. PATENT DOCUMENTS 3,671,523 6/1972 Westphal et al. ....................... 71/93

Primary Examiner—Catherine L. Mills
Attorney, Agent, or Firm—Sprung, Horn, Kramer & Woods

[57] ABSTRACT

A selectively herbicidal composition of matter comprising a herbicidally effective amount of (i) 4-amino-6-tert.-butyl-3-ethylthio-1,2,4-triazin-5(4H)-one, and (ii) at least one of
S-2,3,3-trichloroallyl diisopropyl-thiolcarbamate,
S-2,3-dichloroallyl diisopropyl-thiolcarbamate,
1-amino-6-ethylthio-3-(2,2-dimethylpropyl)-1,3,5-triazine-2,4(1H,3H)-dione,
1,2-dimethyl-3,5-diphenyl-pyrazolium methyl-sulphate,
ethyl N-benzoyl-N-(3,4-dichlorophenyl)-2-amino-propionate,
isopropyl N-benzoyl-N-(3-chloro-4-fluorophenyl)-2-amino-propionate,
methyl N-benzoyl-N-(3-chloro-4-fluorophenyl)-2-amino-propionate,
methyl 2-[4-(2,4-dichlorophenoxy)-phenoxy]-propionate, and
methyl 2-chloro-3-(4-chlorophenyl)-propionate.

Ingredient (i) above as well as the compositions are especially suited for selectively killing monocotyledon and dicotyledon weeds in the cultivation of cereals and leguminous plants.

1 Claim, No Drawings

SELECTIVELY HERBICIDAL 4-AMINO-6-TERT.-BUTYL-3-ETHYLTHIO-1,2,4-TRIAZIN-5(4H)-ONE

The present invention relates to the use of a known 1,2,4-triazin-5-one for selectively combating weeds, and to new herbicidal agents which contain this triazinone derivative in combination with certain other known herbicidally active compounds.

It has already been disclosed that certain 3,6-disubstituted 4-amino-1,2,4-triazin-5-(4H)-ones can be used as herbicides (compare, for example, U.S. Pat. Nos. 3,671,523 and 3,905,801). However, these triazones are not always satisfactory when they are employ for selectively combating weeds. Thus, in practice, most triazinones present difficulties when they are used for selectively combating broad-leaved weeds and graminaceous weeds in cereals. Of the group of triazinones described, 4-amino-6-tert.-butyl-3-methylthio-1,2,4-triazin-5(4H)-one (A) has found acceptance in practice, and is used for selectively combating weeds in soybeans, potatoes, tomatoes and lucerne and, with severe limitations, in cereals. Its use in cereals is based exclusively on post-emergence treatment. It is not possible to use it in cereals by the pre-emergence method for tolerance reasons. In addition, for reasons of phytotoxicity towards the cereal, its use is recommended only with certain varieties of cereal, and even in this case only in a limited area.

It is furthermore already known that 4-amino-6-tert.-butyl-3-ethylthio-1,2,4-triazin-5(4H)-one (B) has general herbicidal properties (compare U.S. Pat. No. 3,671,523). However, particular properties of this compound, in particular possibilities for selective use of this triazinone derivative in crops of useful plants, have not been disclosed.

It has now been found, surprisingly, that 4-amino-6-tert.-butyl-3-ethylthio-1,2,4-triazin-5(4H)-one of the formula

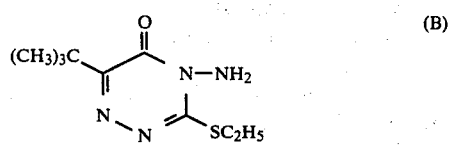

(B)

which is known, is particularly suitable for selectively combating monocotyledon and dicotyledon weeds in cereal crops and leguminous crops before and after emergence of the plants. The use of active compound (B) as a selective herbicide for cereals, chiefly in barley and wheat, is of particular importance.

It is particularly surprisingly that, in the case of the active compound (B) to be used according to the invention—in contrast to the closely related active compound (A)—the difference between the effective herbicidal dose and the dose still tolerated by cereals and leguminosae is relatively large, so that the danger of phytotoxic damage to the crop plants is very slight. In the case of use in cereals, it is furthermore surprising that active compound (B), again in contrast to active compound (A), can be employed not only by the post-emergence method but also by the pre-emergence method; moreover, active compound (B) can also be successfully used by the so-called pre-sowing incorporation method.

These particular properties of active compound (B) enables weeds to be combated in cereals using a herbicidally active triazinone which, at the same time, is well tolerated by the crop plants. The active compound (B) which can be used according to the invention thus represents a great enrichment of selective herbicides in the cultivation of cereals and leguminosae.

By weeds, in the broadest sense, there are to be understood all plants which usually occur as contaminants of cereal crops or leguminosae crops. Examples which may be mentioned of weeds which are destroyed by the triazinone (B) to be used according to the invention and frequently occur in cereal crops and leguminous crops are:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polgonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

However, the use of the active compound (B) according to the invention is in no way restricted to these genera, but also extends in the same manner to other plants.

Active compound (B) is particularly suitable for combating weeds in the wheat, barley and corn varieties of cereal and in the pea and soybean varieties of leguminosae, the action being directed equally towards broadleaved weeds (dicotyledoneae) and towards graminaceous weeds (monocotyledoneae), in particular Avena fatua, Bromus, Alopecurus and Setaria.

It has also been found that new active compound combinations consisting of 4-amino-6-tert.-butyl-3-ethylthio-1,2,4-triazin-5(4H)-one (B) and certain other known herbicidally active compounds have a particularly high herbicidal activity and are outstandingly suitable for broadening the action spectrum and for extending the application range of the triazinone (B).

Thus, active compound combinations consisting of the triazinone (B) on the one hand and (a) S-2,3,3-trichloroallyl diisopropylthiolcarbamate (triallate), (b) S-2,3-dichloroallyl diisopropylthiolcarbamate (diallat) or (c) 1-amino-6-ethylthio-3-(2,2-dimethylpropyl)-1,3,5-triazine-2,4(1H,3H)-dione of the formula

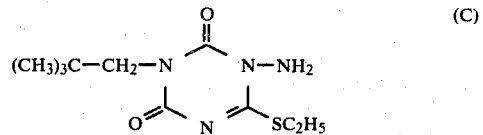

(C)

(compare Danish Patent Specification No. 136,067), on the other hand, can be particularly successfully used by the pre-sowing incorporation method or by the pre-emergence method.

In contrast, in the case of post-emergence treatment, active compound combinations which consist of the triazinone (B) on the one hand and (d) 1,2-dimethyl-3,5- diphenylpyrazolium methyl-sulphate (difenzoquat); (e) ethyl N-benzoyl-N-(3,4-dichlorophenyl)-2-aminopropionate (benzoylprop-ethyl); (f) isopropyl N-benzoyl-N-(3-chloro-4-fluorophenyl)-2-aminopropionate (flampropisopropyl); (g) methyl N-benzoyl-N-(3-chloro-4-fluorophenyl)-2-aminopropionate (flamprop-methyl); (h) methyl 2-[4-(2,4-dichlorophenoxy)-phenoxy]-propionate (diclofopmethyl) or (i) methyl 2-chloro-3-(4-chlorophenyl)-propionate (chlorfenprop-methyl), on the other hand, are preferred. The particularly preferred active compound combination consisting of the triazinone (B) and 1-amino-6-ethylthio-3-(2,2-dimethylpropyl)-1,3,5-triazine-2,4-(1H,3H)-dione (C) can also be used with outstanding success in post-emergence treatment.

Surprisingly, the herbicidal activity of the active compound combinations mentioned is greater than the sum of the actions of the individual components, that is to say the active compound combinations exhibit a synergistic effect. The new active compound combinations thus likewise represent a valuable enrichment of the art.

The weight ratios of the active compounds in the active compound combinations can vary within relatively wide limits. In general, 0.1 to 8 parts by weight of the mixing partner mentioned, preferably 0.2 to 4 parts by weight, are present per part by weight of the triazinone (B).

The active compound combinations according to the invention can be used for the same plants as the active compound (B).

The triazinone (B) and the new active compound combinations mentioned can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is, liquid solvents and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysation products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo-metal phthalocyanine dyestuffs, and trace nutrients such as salts of iron, manganese, boron, copper, cobalt, molybdenum and zinc, as further additives in the formulations.

The formulations in general contain between 0.1 and 95 percent by weight of active compound or active compound combination, preferably between 0.5 and 90%.

The active compound combinations according to the invention are in general used in the form of finished formulations. However, the active compounds contained in the active compound combinations can also be mixed as individual formulations when used, that is to say they can be used in the form of tank mixtures.

The active compound (B) and the new active compound combinations, as such or in the form of their formulations, can also be used as mixtures with other known herbicides for cereals and leguminosae, finished formulations or tank mixing again being possible. Mixtures with other known active compounds, such as fungicides, insecticides, acaricides, nematicides, bird repellents, growth regulators, plant nutrients and agents which improve soil structure, are also possible.

The active compound (B) and the new active compound combinations can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, dusting or scattering.

While the triazinone (A) can be applied to cereals only by the "post-emergence" method, and even then only with the further limitations mentioned, it is possible to apply the triazinone (B) and the above-mentioned new active compound combinations to cereals both by the "post-emergence" method and by the "pre-emergence" method. The triazinone (B) and the new active compound combinations can also be incorporated into the soil before sowing.

The amount of active compound applied can vary within a substantial range, and depends, inter alia, on the weather and on soil factors. In general, the amounts applied are between 0.01 and 5 kg of active compound (B) or active compound combinations per ha, preferably between 0.1 and 3 kg/ha.

The following examples serve to illustrate the invention.

EXAMPLE 1

4-Amino-6-tert.-butyl-3-ethylthio-1,2,4-triazin-5(4H)-one (B)

5 ml of an alkylaryl polyglycol ether, as an emulsifier, and 572 g (5.25 mols) of ethyl bromide are added to a solution of 1,000 g (5 mols) of 4-amino-6-tert.-butyl-3-mercapto-1,2,4-triazin-5(4H)-one (compare U.S. Pat. No. 3,671,523) in 5,250 ml of 1 N sodium hydroxide solution. The mixture is stirred vigorously at 50° C. until the pH value of the aqueous phase has fallen to 7-8 (10-12 hours). After cooling the mixture to 20° C., the reaction product which has crystallized out is filtered off, washed several times with water and dried at 50° C. 1,050 g (92% of theory) of an isomer mixture which has a melting point of 77°-82° C. and the following composition, determined by gas chromatography, are obtained:

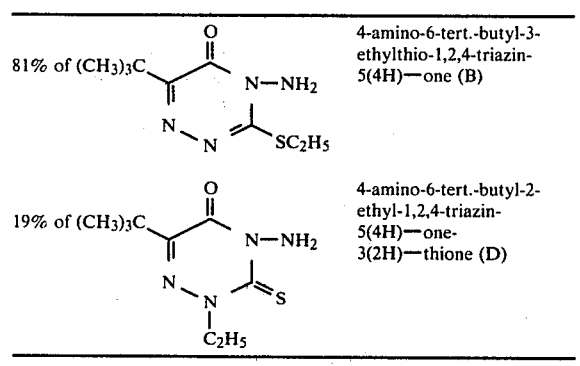

The pure 3-ethylthio derivative (B) with a melting point of 95° C. can easily be separated off by recrystallizing the isomer mixture from cyclohexane.

If, instead of ethyl bromide, the equivalent amount of ethyl iodide is used, the two isomers (B) and (D) are formed in a ratio of 90:10.

FORMULATION EXAMPLE

A 60% strength wettable powder is prepared by the following procedure: 60 parts by weight of the triazinone (B), consisting of technical grade active compound, 3 parts by weight of an arylalkylsulphonate, 3 parts by weight of sulphite waste liquor (spray-dried), 5 parts by weight of a formaldehyde/cyclohexanone/Na bisulphite condensate, 10 parts by weight of highly dispersed silicic acid and alumina (as the remainder to make up to 100 parts by weight) are mixed in a Lödiger mixer and the mixture is then ground via an 8 inch jet mill.

The formulation thus prepared can be suspended in water and is used for the preparation of a ready-to-use spray formulation.

USE EXAMPLES

In all the examples:
(A) = 4-amino-6-tert.-butyl-3-methylthio-1,2,4-triazin-5(4H)-one
(B) = 4-amino-6-tert.-butyl-3-ethylthio-1,2,4-triazin-5(4H)-one Explanation of the abbreviations:
PANMI = *Panicum miliaceum*
SINAL = *Sinapis alba*
GASPA = *Galinsoga parviflora*
STEME = *Stellaria media*
CHEAL = *Chelopodium album*
LAMSS = *Lamium spec.*
POLCO = *Polygonum convolvulus*
POLLA = *Polygonum lapathifolium*
VIOTR = *Viola tricolor*
RAPRA = *Raphanus raphanistrum*
GALAP = *Galium aparine*
POLAV = *Polygonum aviculare*

EXAMPLE 2

Post-emergence test/greenhouse
Solvent: 5 parts by weight of acetone
Emulsifier: 1 part by weight of alkylaryl polyglycol ether To produce a suitable preparation of active compound, 1 part by weight of active compound is mixed with the state amount of solvent, the stated amount of emulsifier is added and the concentrate is diluted with water to the desired concentration.

Test plants which have a height of 5-15 cm are sprayed with the preparation of the active compound in such a way as to apply the amounts of active compound per unit area which are indicated in the table. The concentration of the spray liquor is so chosen that the amounts of active compound shown in the table are applied in 2,000 l of water/ha. After three weeks, the degree of damage to the plants is rated in % damage in comparison with the development of the untreated control. The figures denote:

0% = no action (like untreated control)
100% = total destruction

The active compounds, amounts applied and results can be seen from the following Table A:

TABLE A

| | Post-emergence test/greenhouse | | | | | | |
|---|---|---|---|---|---|---|---|
| Active compound | Amount of active compound applied kg/ha | PANMI | SINAL | GASPA | STEME | Wheat | Corn |
| (A) | 1.0 | 100 | 100 | 100 | 100 | 100 | 90 |
| | 0.5 | 100 | 100 | 100 | 100 | 90 | 90 |
| | 0.25 | 100 | 100 | 100 | 100 | 90 | 70 |
| (B) | 1.0 | 100 | 100 | 100 | 100 | 20 | 80 |
| | 0.5 | 100 | 100 | 100 | 100 | 0 | 20 |
| | 0.25 | 95 | 100 | 100 | 90 | 0 | 0 |

EXAMPLE 3

Post-emergence test/open-air

In a multi-crop test, summer wheat, summer barley and peas were sown on sandy loam with a medium humus content. Sowing took place on May 8. Treatment with the herbicide was carried out after 33 days, on June 10th, that is to say by the post-emergence method. At the time of treatment, the weeds were in the 4-6 leaf stage. The amounts of active compound indicated were applied in 500 l of water/ha. The acitve compounds were triazinone (A), formulated as a 70% strength wettable powder, and triazinone (B), formulated as a 60% strength wettable powder. The plot size was 10 m². The herbicidal action was measured on the naturally occuring weed population. The action on the weeds and crops was determined in percentage damage in comparison with the untreated control and is summarized in the following Table B:

TABLE B

| Active compound | Amount of active compound applied kg/ha | CHEAL | RAPRA | GALAP | POLCO | POLAV | Summer barley | Summer wheat | Peas |
|---|---|---|---|---|---|---|---|---|---|
| (A) | 2.0 | 100 | 100 | 90 | 100 | 100 | 95 | 70 | 70 |
|  | 1.5 | 100 | 100 | 85 | 100 | 100 | 90 | 50 | 50 |
|  | 1.0 | 100 | 100 | 80 | 100 | 100 | 85 | 30 | 30 |
|  | 0.5 | 100 | 100 | 75 | 100 | 100 | 30 | 10 | 10 |
| (B) | 2.0 | 100 | 100 | 100 | 100 | 100 | 10 | 0 | 15 |
|  | 1.5 | 100 | 100 | 95 | 100 | 100 | 5 | 0 | 10 |
|  | 1.0 | 100 | 100 | 90 | 100 | 100 | 0 | 0 | 5 |
|  | 0.5 | 100 | 100 | 80 | 100 | 100 | 0 | 0 | 0 |

EXAMPLE 4

Pre-emergence test/greenhouse

In a greenhouse test, the reaction of various varieties of cereal towards herbicides was examined in seed dishes. Seed dishes (20×20 cm in size) were filled with sandy loam with a humus content of 2.2%. After sowing the various varieties of cereal, spraying took place in a spray booth on the same day, that is to say by the pre-emergence method. The amount of active compound was applied in 420 l of water/ha. Evaluation took place 4 weeks after sowing. The action was rated as percentage damage in comparison with the untreated control and is summarized in the following Table C:

TABLE C

| Active compound | Amount of active compound applied kg/ha | Pre-emergence test/greenhouse |  |  |  |  |  |
|---|---|---|---|---|---|---|---|
|  |  | Wheat |  |  | Barley |  |  |
|  |  | Neepawa | Triumph | Wascana | Larker | Bonanza | Galt |
| (A) | 0.5 | 87 | 100 | 100 | 100 | 97 | 100 |
|  | 0.25 | 17 | 60 | 63 | 25 | 10 | 17 |
|  | 0.125 | 0 | 2 | 10 | 3 | 2 | 8 |
| (B) | 0.5 | 0 | 2 | 18 | 3 | 8 | 12 |
|  | 0.25 | 0 | 0 | 10 | 0 | 0 | 10 |
|  | 0.125 | 0 | 0 | 2 | 0 | 0 | 0 |

EXAMPLE 5

Pre-emergence test/open-air

In a multi-crop test, summer wheat, summer barley and peas were sown on sandy loam with a medium humus content. Sowing took place on May 8th Treatment with the herbicide took place the same day, that is to say by the pre-emergence method. The amounts of active compound indicated were applied in 500 l of water/ha. The active compounds were triazinone (A), formulated as a 70% strength wettable powder, and triazinone (B), formulated as a 60% strength wettable powder. The plot size was 10 m². The herbicidal action was measured on the naturally occuring weed population. The action on weeds and crops was determined in percentage damage in comparison with the untreated control and is summarized in the following Table D:

TABLE D

| Active compound | Amount of active compound applied kg/ha | Pre-emergence test/open-air |  |  |  |  |  |
|---|---|---|---|---|---|---|---|
|  |  | CHEAL | LAMSS | POLCO | Summer barley | Summer wheat | Peas |
| (A) | 2,0 | 100 | 100 | 100 | 50 | 30 | 70 |
|  | 1,5 | 100 | 100 | 100 | 30 | 10 | 50 |
|  | 1,0 | 100 | 95 | 100 | 20 | 5 | 30 |
|  | 0,5 | 95 | 90 | 95 | 10 | 0 | 10 |
| (B) | 2.0 | 95 | 100 | 100 | 10 | 10 | 10 |
|  | 1.5 | 90 | 100 | 100 | 0 | 0 | 0 |
|  | 1.0 | 85 | 95 | 95 | 0 | 0 | 0 |
|  | 0.5 | 75 | 80 | 90 | 0 | 0 | 0 |

EXAMPLE 6

Pre-emergence test/open-air

In a multi-crop test, summer wheat, summer barely and peas were sown on sandy loam with a medium humus content. Sowing took place on May 20th treatment with the herbicide was carried out on the following day, that is to say by the pre-emergence method. The amounts of active compound indicated were applied in 500 l water/ha. The active compounds were triazinone (A), formulated as a 70% strength wettable powder, and triazinone (B), formulated as a 60% strength wettable powder. The plot size was 10 m². The herbicidal action was measured on the naturally occuring weed population. The action on weeds and crops was determined in percentage damage in comparison with the untreated control and is summarized in the following Table E:

TABLE E

| | | Pre-emergence test/open-air | | | | | | |
|---|---|---|---|---|---|---|---|---|
| Active compound | Amount of active compound applied kg/ha | POLLA | VIOTR | LAMSS | POLCO | Summer barley | Summer wheat | Peas |
| (A) | 2.0 | 100 | 100 | 100 | 100 | 50 | 50 | 5 |
| | 1.5 | 98 | 100 | 100 | 95 | 20 | 30 | 0 |
| | 1.0 | 95 | 98 | 95 | 90 | 10 | 20 | 0 |
| | 0.5 | 85 | 95 | 90 | 85 | 5 | 10 | 0 |
| (B) | 2.0 | 100 | 100 | 100 | 100 | 0 | 0 | 0 |
| | 1.5 | 100 | 95 | 100 | 95 | 0 | 0 | 0 |
| | 1.0 | 95 | 90 | 95 | 90 | 0 | 0 | 0 |
| | 0.5 | 85 | 70 | 85 | 80 | 0 | 0 | 0 |

EXAMPLE 7

Pre-sowing incorporation/greenhouse

In a greenhouse test, the reaction of various varieties of cereal towards herbicides was examined in seed dishes. Seed dishes (20×20 cm in size) were filled with sandy loam with a humus content of 2.2%. Spraying took place in a spray booth. The amounts of active compound were applied in 420 l of water/ha. After the spraying, the active compound was incorporated into the soil and the various varieties of cereal were then sown. Application thus took place by the presowing incorporation method. Evaluation took place 4 weeks after sowing. The action was rated as percentage damage in comparison with the untreated control and is summarized in the following Table F:

TABLE F

| | | Pre-sowing incorporation/greenhouse | | | | | |
|---|---|---|---|---|---|---|---|
| | Amount of active compound applied | Wheat | | | Barley | | |
| Active compound | kg/ha | Neepawa | Triumph | Wascana | Larker | Bonanza | Galt |
| (A) | 0.5 | 100 | 100 | 100 | 100 | 100 | 100 |
| | 0.25 | 25 | 57 | 90 | 75 | 63 | 17 |
| | 0.125 | 3 | 15 | 27 | 12 | 17 | 8 |
| (B) | 0.5 | 8 | 15 | 8 | 3 | 8 | 12 |
| | 0.25 | 3 | 5 | 0 | 0 | 0 | 10 |
| | 0.125 | 0 | 0 | 0 | 0 | 0 | 0 |

EXAMPLE 8

Individual field plots were treated with the herbicides A and B, respectively, 4-amino-6-tert.-butyl-3-methylthio-1,2,4-triazin-5(4H)-one and its 3-ethylthio homologue, by applying them broadcasting over the soil surface at various kg/hectare rates and immediately rototilling them in to a depth of approximately 4 inches. On the same day, wheat and barley were planted rowwise into the plots.

| Abbreviation | Botanical Name | Common Name |
|---|---|---|
| AMARE | Amaranthus retroflexus | Red Root Pig Weed |
| AMBEL | Ambrosia artemisiifolia | Rag Weed |
| AVEFA | Avena fatua | Wild Oat |
| BRAPI | Brachiaria piligera | None |
| CHEAL | Chenopodium album | Lambs Quarters |
| DATST | Datura stramonium | Jimson Weed |
| DIGSA | Digitaria sanguinalis | Large Crab Grass |
| ECHCG | Echinochloa crus-galli | Barnyardgrass |
| GAETE | Galeopsis tetrahit | Hemp nettle |
| HELAN | Helianthus annuus | Sunflower |
| POLPE | Polygonum persicaria | Redshank |
| POLSC | Polygonum scabrummoench | Green Smartweed |
| SETVI | Setaria viridis | Green Foxtail |

Four weeks later evaluations were made visually in comparison to adjacent untreated CHECK plots with respect to the amount of damage. Each weed evaluation was based on four combined plots receiving the same concentration of herbicide. For each crop there was determined that concentration of herbicide which produced at most 15% damage. For each weed there was determined that concentration of herbicide which produced at least 80% control.

Table G and H present the results for each herbicide with respect to both crops and weeds. The vertical lines represent the acceptable concentration for each crop and "X" to the right of such line for any given weed means the weed is not controlled at a concentration suitable for that crop. If "X" is to the left of the vertical, it means the weed is controlled.

The longer the horizontal line is to the left of the vertical line, the greater is the margin of safety in using the particular herbicide.

These tables show that the 3-ethylthio homologue with these crops is superior to the 3-methylthio homologue.

TABLE G

WHEAT

| Weed | Rate of Pre-emergent application, Kg/ha B | A |
|---|---|---|
| | .25 \| .375 \| .5 \| .75 \| 1.0 \| 1.25 \| 1.5 \| 2.0 \| 3.0 \| 4.5 | .1 \| .15 \| .2 \| .25 \| .375 \| .5 \| .75 \| 1.0 \| 1.25 \| 1.5 |
| AVEFA SETVI AMARE CHEAL | (bar chart data) | (bar chart data) |
| AVEFA AMARE CHEAL POLSC (GAETE) | (bar chart data) | (bar chart data) |
| AVEFA BRAPI (DIGSA) (ECHCG) AMARE AMBEL CHEAL DATST HELAN | (bar chart data) | (bar chart data) |
| AVEFA SETVI CHEAL | (bar chart data) | (bar chart data) |
| AVEFA AMARE CHEAL POLSC | (bar chart data) | (bar chart data) |
| AVEFA POLPE | (bar chart data) | (bar chart data) |
| AVEFA SETVI POLPE | (bar chart data) | (bar chart data) |

The vertical line indicates the rate at which damage to the crop was within acceptable limits, i.e., no more than 10-15%.

"X" indicates the rate at which each individual weed was controlled to a commercially acceptable degree, i.e., about 80%.

If the letter "X" is on the vertical line, commercial control of that weed was achieved at the highest, still tolerable rate. If the letter "X" appears to the left of the vertical line, weed control was achieved at a lower rate that the crop tolerance limit. The horizontal connecting line between "X" and the vertical indicates selective weed control, and the length of the line reflects the margin of safety.

TABLE H

BARLEY

Rate of Pre-emergent application, Kg/ha

| WEED | B | | | | | | | | | A | | | | | | | | |
|---|---|---|---|---|---|---|---|---|---|---|---|---|---|---|---|---|---|---|
| | .25 | .375 | .5 | .75 | 1.0 | 1.25 | 1.5 | 2.0 | 3.0 | .1 | .15 | .2 | .25 | .375 | .5 | .75 | 1.0 | 1.25 | 1.5 |
| AVEFA SEIVI AMARE CHEAL | | | | | X | | | X | X X | | | | | | | | | | X X X X |
| AVEFA AMARE CHEAL POLSC GAETE | | X X X X X | | | | | | | | X | | | | X X X X X | | X | | |
| (AVEFA) (SEIVI) CHEAL | | | X | | X | X | | | | | | | X | | | X X X | | |
| AVEFA AMARE CHEAL POLSC | | | X X X | X | | | | | | | | X X X X | | | | | | |
| AVEFA POLPE | | X | | X | X | | | | | | | X X | | | | | | |
| AVEFA (SEIVI) POLPE | | | | X X | | | | | | | | | | | | X X X | | |

The vertical line indicates the rate at which damage to the crop was within acceptable limits (no more than 10–15%).

"X" indicates the rates at which each individual weed was controlled to a commercially acceptable degree (about 80%).

If the letter "X" is on the vertical line, commercial control of that weed was achieved at the highest, still tolerable rate. If the letter "X" appears to the left of the vertical line, weed control was achieved at a lower rate than the tolerance limit. The horizontal connecting line between "X" and the vertical is then indicative for selective weed control, and the length of the line reflects the margin of safety.

It will be understood that the specification and examples are illustrative but not limitative of the present invention and that other embodiments within the spirit and scope of the invention will suggest themselves to those skilled in the art.

What is claimed is:

1. A process for selectively killing monocotyledon and dicotyledon weeds in the cultivation of cereal and leguminous crops comprising applying to the crops or to a habitat thereof a selectively weed-herbicidally effective amount of (i) 4-amino-6-tert.-butyl-3-ethylthio-1,2,4-triazin-5 (4H)one.

* * * * *